United States Patent
Dahlem (10) Patent No.: US 7,284,857 B1
(45) Date of Patent: Oct. 23, 2007

(54) APPARATUS AND METHOD FOR TREATING LEARNING DIFFERENCES

(76) Inventor: Robert E. Dahlem, 12209 Saratoga Estates Rd., Louisville, KY (US) 40299

( * ) Notice: Subject to any disclaimer, the term of this patent is extended or adjusted under 35 U.S.C. 154(b) by 392 days.

(21) Appl. No.: 10/985,697

(22) Filed: Nov. 11, 2004

Related U.S. Application Data (60) Provisional application No. 60/518,681, filed on Nov. 11, 2003.

(51) Int. Cl.
*A61B 3/00* (2006.01)
(52) U.S. Cl. .................. 351/203; 351/204; 351/170; 351/175
(58) Field of Classification Search ............ 351/201, 351/202, 204, 216, 219, 233, 170, 175, 203, 351/159; 600/558; 359/625, 640, 678, 720
See application file for complete search history.

(56) References Cited

U.S. PATENT DOCUMENTS

| | | | |
|---|---|---|---|
| 3,842,822 A | 10/1974 | Levinson et al. | |
| 3,906,644 A | 9/1975 | Levinson et al. | |
| 3,955,564 A | 5/1976 | Levinson et al. | |
| 4,379,699 A | 4/1983 | Nelson | |
| 4,698,564 A * | 10/1987 | Slavin | 318/257 |
| 4,979,902 A | 12/1990 | Morelle et al. | |

\* cited by examiner

*Primary Examiner*—Hung X. Dang
*Assistant Examiner*—Joseph Martinez
(74) *Attorney, Agent, or Firm*—Stites & Harbison, PLLC; David W. Nagle, Jr.; Mandy W. Decker (57) ABSTRACT

A method for treating a learning difference of an individual, comprises predicting an eclipsed area of a retina of an eye of the individual; providing a prism lens having dimensions selected for directing light to the eclipsed area; and positioning the prism lens adjacent the eye such that light is directed to the eclipsed area of the retina, thereby alleviating symptoms of the learning difference. The apparatus includes a prism lens for directing light to an eclipsed area of a retina of an eye of the individual and means for positioning said prism lens adjacent the eye such that light is directed to the eclipsed area of the retina to address the learning difference.

21 Claims, 9 Drawing Sheets

APPARATUS AND METHOD FOR TREATING LEARNING DIFFERENCES

CROSS REFERENCES TO RELATED APPLICATIONS

This application claims priority from U.S. Provisional Application Ser. No. 60/518,681 filed Nov. 11, 2003, the entire disclosure of which is incorporated herein by this reference.

BACKGROUND OF THE INVENTION

When light enters an eye, it is refracted as it moves through the cornea, and again when it moves through the lens, before being reflected by the retina. The retina is composed of photoreceptors, which convert light to electrical impulses for passage through the optic nerve to the visual cortex of the brain where the sensation of vision occurs.

The retina contains cones, which are responsible for color vision, and rods, which are responsible for vision in the dark and black and white contrast. Photoreceptors are bundled together and communicate with a specific area of the visual cortex and later pass through optic radiation (a fiber system extending between the thalamus and the visual cortex) by way of a magnocellular pathway and a parvocellular pathway to the rear of the brain.

The magnocellular pathway and the parvocellular pathway (sometimes collectively referred to herein as "optic pathways") are associated with rods and cones, respectively, and are involved in perception of 3-D positioning, spatial orientation, and the ability to read, write, recognize words, and decipher meanings of words.

Indeed, irregularities in the magnocellular and parvocellular pathways, as well as the back left portion of the brain, have being implicated in cases of learning differences, such as difficulty reading, writing, recognizing words, and deciphering the meanings of words. For example, pathologists have found damage to the magnocellular and parvocellular pathways in dyslexic individuals. Additionally, neuroimaging equipment has helped researchers identify the back left part of the brain as the portion that allows for reading.

It has been suggested that learning differences, such as dyslexia, are not generally the result of brain damage or abnormality, but the result of the eyes inability to send data through the optic pathways to the parts of the brain which are used during reading. There is not currently known to be an apparatus or method which could correct such errors. Accordingly, there remains a need in the art for an apparatus and method which satisfactorily addresses the above mentioned problems.

SUMMARY OF THE INVENTION

The present invention meets the above identified needs, and others, by providing an apparatus and method for treating learning differences by redirecting electromagnetic radiation (also referred to herein as "light") as it enters the eye, thereby alleviating symptoms of the learning differences.

Without wishing to be bound by theory or mechanism, it is thought that facial asymmetry is present in certain individuals having learning differences, including sensory perception disorders such as dyslexia. This facial asymmetry may result in a shifting in a lens of at least one eye of the individual, causing light entering the eye to be directed only to certain areas of the retina, leaving one or more eclipsed areas. As such, the brain receives incompatible data from the two eyes of the individual. While the brain attempts to fuse the two sets of data, interference patterns of excitation in the visual cortex occur. Such compensation by the visual cortex includes blocking or processing the data in alternate manners which may lead to delays and errors, resulting in symptoms associated with learning differences, such as dyslexia. By redirecting the light entering the eye having the shifted lens using the apparatus and method of the present invention, the eclipsed areas of the retina becomes activated, thereby alleviating the symptoms of the learning difference.

An exemplary apparatus of the present invention includes a prism lens placed adjacent the eye such that light entering the eye is redirected. Light entering the eye with the aide of the prism lens is directed toward the eclipsed area. Because the eclipsed area of the retina could vary depending, for example, on the degree of facial asymmetry, which is thought to correlate to a particular type of learning difference, the prism lens may be designed to direct light specifically to the eclipsed area of the retina of the individual being treated.

An exemplary method of the present invention includes: predicting an eclipsed area of a retina of an eye of the individual; providing a prism lens having dimensions selected for directing light to the eclipsed area; and positioning the prism lens adjacent the eye.

Predicting an eclipsed area of a retina of an eye involves identifying the eye having a shifted lens. In this regard, the non-dominant eye in a binocular viewing environment tends to be the eye having a shifted lens and therefore an eclipsed area of the retina. Once the eclipsed area is predicted, a prism lens is selected having an angle to redirect light to the eclipsed area. The angle and orientation of the lens for redirecting light entering the eye of the individual being treated will vary depending on the location of the eclipsed area of the retina. Lenses having varying angles may be tested on the individual until one is identified which has a beneficial result, e.g., in the case of certain forms of dyslexia, individuals may experience enhanced "blue" color perception and recognition and enhanced reading and comprehension skills.

Some results may be experienced immediately upon use of the prism lens and other results may be experienced after extended use of the prism lens. As an alternative, or in addition to trial-and-error-based selection of a prism lens angle, a standard curve plotting prism angle as a function of facial asymmetry ratio may be used. The facial asymmetry ratio of the individual being treated may be measured and used to select the prism angle to be used.

The prism lens provided is then placed adjacent the eye with the eclipsed area of the retina. The prism lens should be oriented such that it tends to direct light toward the eclipsed area of the retina. When the photoreceptors in the eclipsed area are activated, a signal from the eye receiving the lens becomes compatible or synchronous with the signal transmitted by the other eye. As such, the brain begins receiving compatible data from the two eyes of the individual and no longer must attempt to fuse two incompatible sets of data. Such synchronicity of data alleviates any previously experienced interference patterns of excitation in the visual cortex which resulted in symptoms associated with learning differences.

DETAILED DESCRIPTION OF THE INVENTION

The present invention is an apparatus and method for treating learning differences by redirecting electromagnetic radiation (referred to hereinafter as "light") as it enters the eye, thereby alleviating the learning differences.

Without wishing to be bound by theory or mechanism, it is thought that facial asymmetry is present in certain individuals having learning differences, including sensory perception disorders such as dyslexia. This facial asymmetry may result in a shifting in a lens of at least one eye of the individual. Because the lens is shifted, light entering the eye is directed such that it only reaches certain areas of the retina, leaving one or more eclipsed areas. As such, the brain receives incompatible data from the two eyes of the individual. While the brain attempts to fuse the two sets of data, interference patterns of excitation in the visual cortex occur. Such compensation by the visual cortex includes blocking or processing the data in alternate manners which may lead to delays and errors, resulting in symptoms associated with learning differences. The present invention is an apparatus and method for redirecting the light entering the eye having the shifted lens, activating the eclipsed areas of the retina, thereby alleviating the problems associated with the presence of an eclipsed area and the delivery of incompatible data to the brain.

Figure 1:
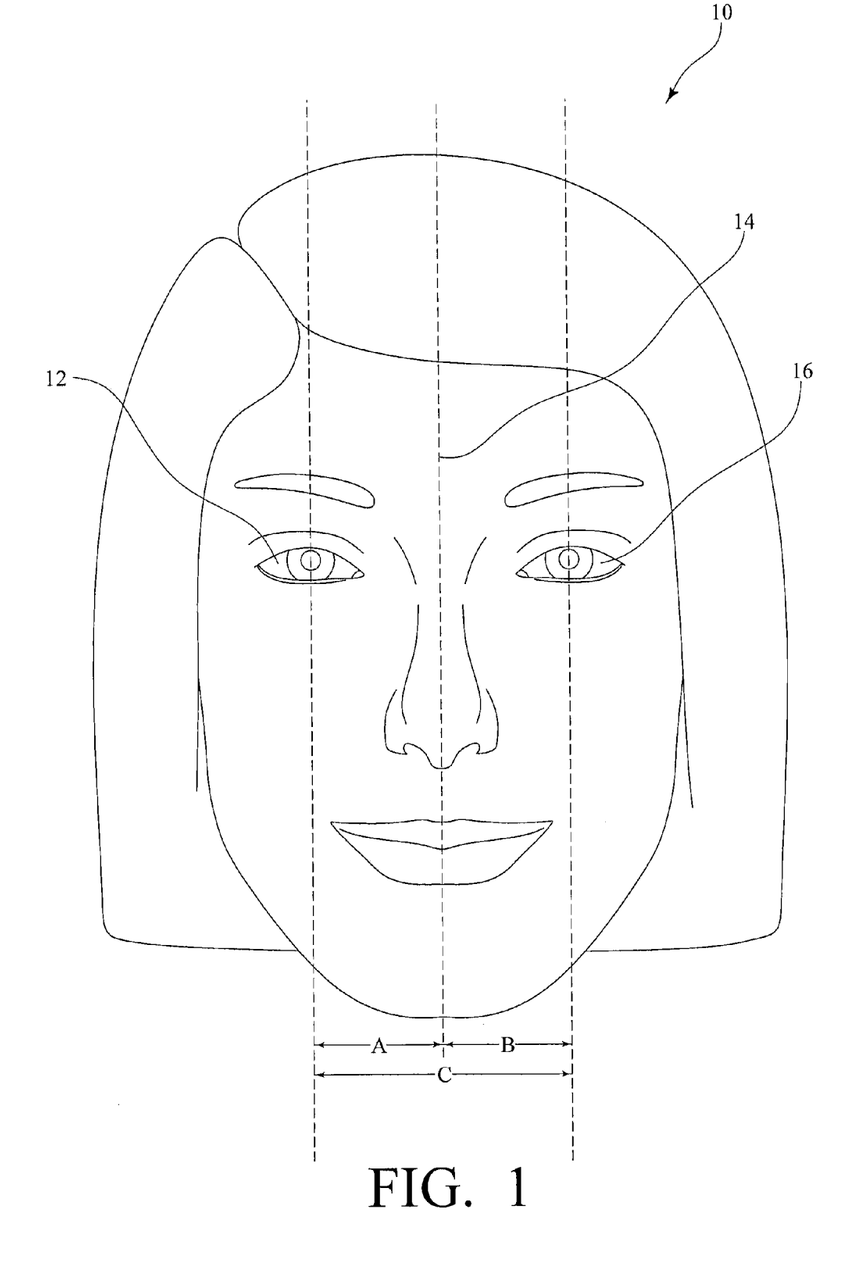
FIG. 1 is a schematic view of a face of an individual.

With reference to FIG. 1, facial asymmetry of an individual 10 may be described using a facial asymmetry ratio (R), calculated using the following equation:

$$R = \frac{A - B}{C} \quad \text{(I)}$$

where,

A is the distance between the pupil of the right eye 12 and the facial midline 14;

B is the distance between the pupil of the left eye 16 and the facial midline 14; and C is the distance between the pupil of the right eye 12 and the pupil of the left eye 16. Facial asymmetry is present in an individual 10 when R is not equal to zero, i.e., when distance A differs from distance B.

Figure 2A:
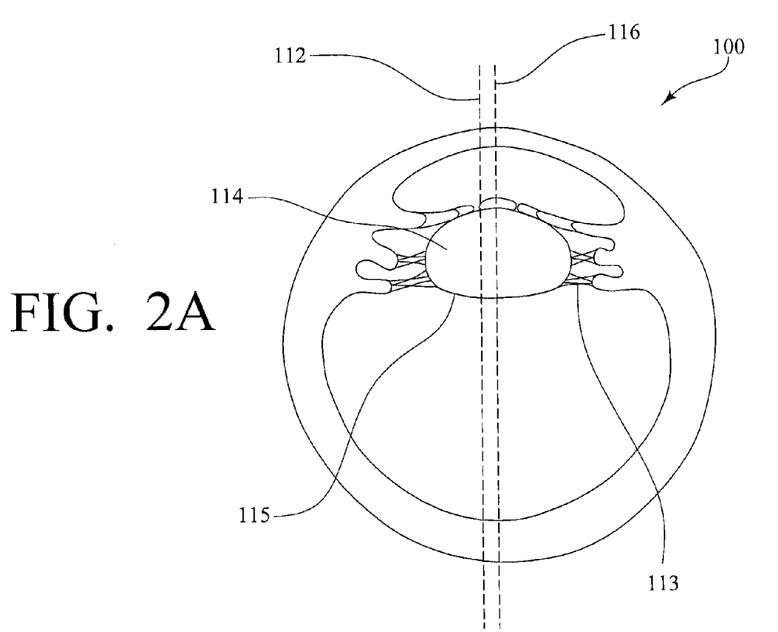
FIG. 2A is a cross-sectional representation of a normal eye.
Figure 2B:
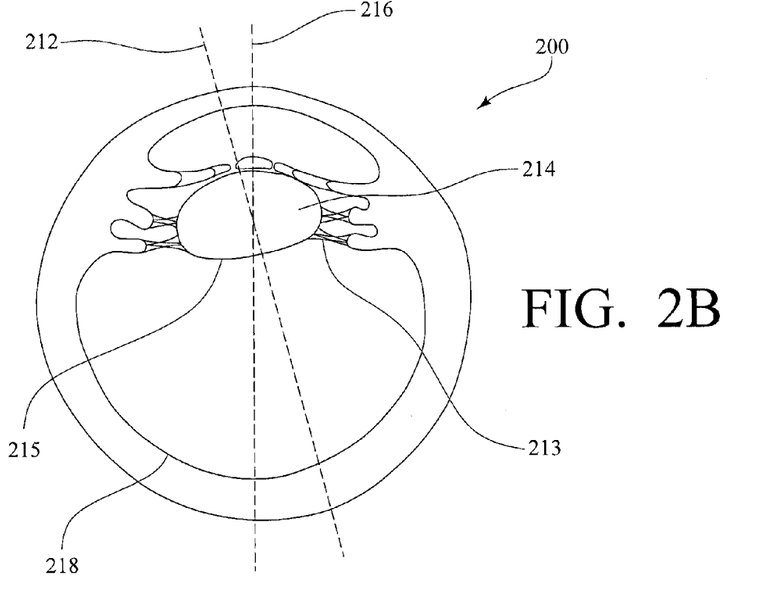
FIG. 2B is a cross-sectional representation of an eye having a shifted lens.

With reference to FIGS. 1, 2A and 2B, it is thought that facial asymmetry may cause a shifting in a lens 114, 214 of at least one eye of the individual 10. In addition to the internal shifting of the lens 114, 214, there may be a horizontal strabismus. The internal shifting of the lens 114, 214 may occur because of a difference in distance A and distance B, resulting in the muscles in the respective regions differing in size or relative location causing the lens 214 to be shifted out of alignment. The shifting of the lens 114, 214 may be affected by the autonomic nervous system controlling zonules 113, 213 attached to the lens capsule 115, 215, which may move the lens 114, 214, intraocularly, by involuntary muscle movement controlled by the nervous system.

With reference to FIG. 2A, in a normal eye 100, the principal axis 112 of the lens 114 is substantially in alignment with the optic axis 116 of the eye 100. However, with reference to FIG. 2B, in an eye 200 having a shifted lens 214, the principal axis 212 of the lens 214 is not in alignment with the optic axis 216 of the eye 200. As such, the shifted lens 214 directs light entering the eye 200 such that it only reaches certain areas of the retina 218.

Figure 3A:
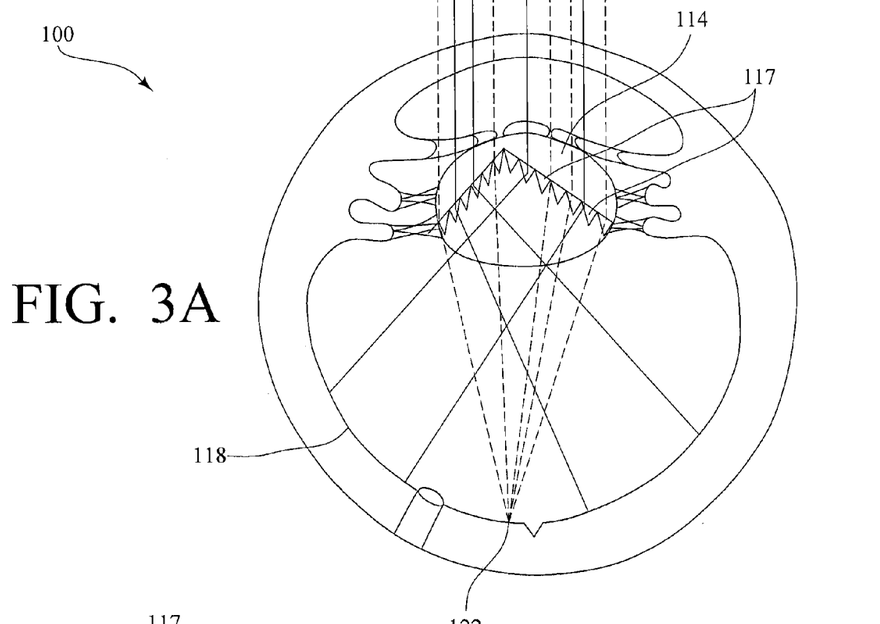
FIG. 3A is a cross-sectional representation of a normal eye, illustrating the movement of light through the lens to various portions of the retina and to the focal point.
Figure 3B:
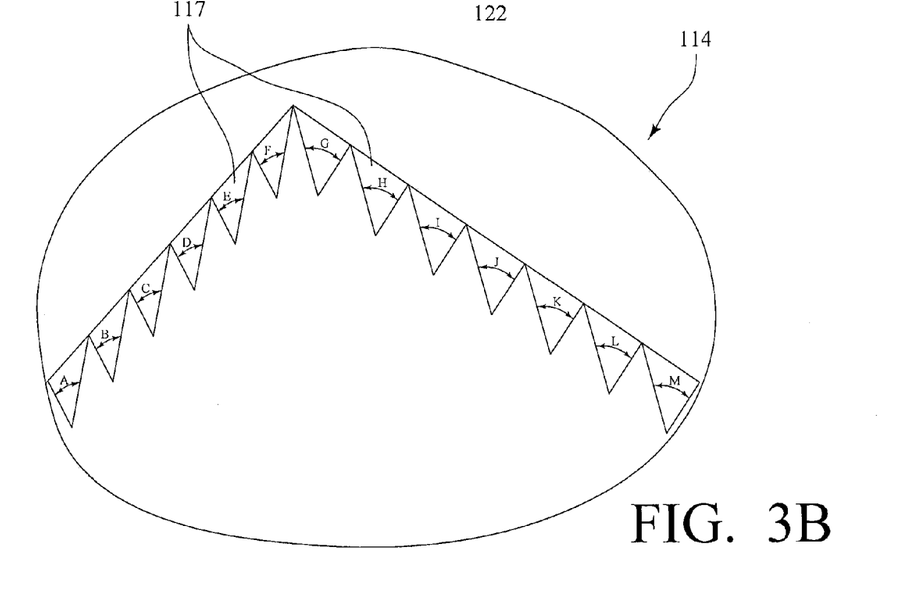
FIG. 3B is an enlarged view of the lens of the eye of FIG. 3A.

Light is thought to be directed to various portions of the retina 118 of a human eye in a manner which does not necessarily require the light to pass through one of the focal points or the center of the lens, i.e., the light may be bent as it passes through the lens and is directed to the retina. If the light is bent, in addition to its simple-lens-like properties, i.e., its ability to direct light based on its focal points, the lens of the human eye has prism-like properties. With reference to FIGS. 3A and 3B, it is thought that the lens 114 acts as a stacked series of prisms 117 to bend light in a manner that directs it to various portions of the retina 118, as illustrated by the solid lines, while also tending to direct light to a focal point 122, as illustrated by the dotted lines.

A structure in the human eye 100 that acts as the stacked series of prisms is thought to be crystalline, formed by osmotically-fed sugar from the aqueous humor. The lens 114 floats in an anterior chamber of the eye and has associated lens fibers, which tend to outline the shape of a prism. See, Leeson & Leeson, "Chapter 20, Organs of Special Senses," *Histology*, 3d Ed., p. 554 (1976), which is incorporated herein by this reference. A cementing substance between the fibers, having substantially the same refractive index as the fibers, creates the stacked-prism-like structure. See, Id.

Figure 4A:
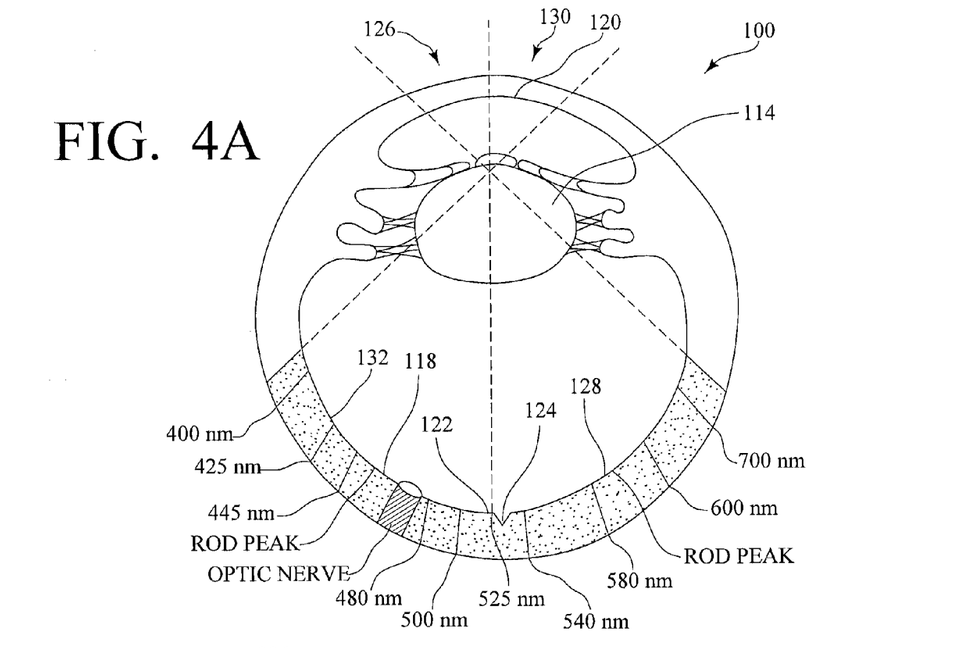
FIG. 4A is a cross-sectional representation of normal eye, illustrating the areas of the retina capable of receiving light.

Turning to FIG. 4A, when light enters a normal eye 100, it is refracted as it enters the cornea 120 and moves through the lens 114 before being reflected by the retina 118. Light entering the normal eye 100 is directed to a focal point 122, medial to the fovea 124, and to normal areas of the retina 118. Light entering from a nasal field 126 (portion closest to the nose) is generally directed to a temporal portion 128 of the retina 118. Similarly, light entering from a temporal field 130 (portion closest to the temple) is generally directed to a nasal portion 132 of the retina 118. The retina 118 is composed of photoreceptors, which convert light to electrical impulses for passage through the optic nerve to the visual cortex of the brain where the sensation of vision occurs.

In order to study the manner in which light is directed through a lens to a retina, a 24× scale model of the human eye was constructed. With reference to FIGS. 3A and 3B, the dimensions of the lens 114 for the 24× scale model were chosen by first identifying a focal point 122 on the retina 118 of the model, which is approximately 0.75 mm medial to a fovea 124 in color vision animals, and therefore approximately 18 mm medial to the fovea 124 in the model. See, Slatter, "Structure and Function of the Eye: The Visual Pathway," *Fundamentals of Veterinary Ophthalmology 2d Ed.* pg. 5 (1990); Guyton, "Chapter 50 The Eye: Receptor and Neural Function of the Retina," *Medical Physiology 8th Ed.* pg. 546 (1991), which are incorporated herein by this reference.

A movable lens 114 was then constructed with stacked prisms 117 made from transparent acrylic. The stacked prisms 117 were selected and tested together by trial and error until the final dimensions were identified, which direct light from a laser to the identified focal point 122. With reference to FIG. 3B, the dimensions of each prism chosen for the model, from medial to lateral, were approximately as follows: A≈13°; B≈11.5°; C≈10°; D≈8°; E≈6°; F≈1.5°; G≈1.5°; H≈4°; I≈6°; J≈8.5°; K≈12.5°; L≈15°; and M≈19°. It should be noted that the lens shown in FIG. 3B is merely a schematic of the lens, designed to facilitate explanation, and not necessarily representative of the actual structural features of a human lens.

In any event, once the dimensions of the lens 114 for the model were selected, light from the laser was directed into the model to determine the area of the retina 118 that receives the light in a normal eye 100. The lens was then shifted to simulate the proposed shifting of a lens in an individual having facial asymmetry. For example, it is thought that in individuals having certain forms of dyslexia, the lens of the right eye is shifted approximately 24 to 25 degrees medial to the optic axis. As such, to simulate the refraction pattern of light on the retina of an individual having such a form of dyslexia, the lens of the 24× scale model was shifted approximately 24-25 degrees medial to the optic axis of the eye. When the lens was so shifted and light from a laser was directed into the model, it was determined that an area medial to the optical nerve becomes eclipsed.

Turning back to FIG. 4A, the crystalline lens 114 it is thought to refract light to locations on the retina 118 containing certain of the photoreceptor cells known as cones, which recognize particular wavelengths of light and therefore particular colors. With continued reference to FIG. 4A, light entering from the temporal field 130 is directed to the nasal portion 132 of the retina 118, medial to the fovea 124, containing photoreceptors recognizing wavelengths from approximately 400 nm to approximately 525 nm, and therefore violet, indigo, blue, blue/green and certain higher frequency greens. Similarly, light entering from the nasal field 126 is directed to the temporal portion 128 of the retina 118, lateral to the fovea 124, containing photoreceptors recognizing wavelengths from approximately 525 nm to approximately 700 nm, and therefore certain lower frequency greens, green/yellow, yellow, orange, and red. Although FIG. 4A depicts a right eye, it is thought that the left eye has a mirror image distribution of photoreceptors recognizing particular wavelengths. That is to say that, like the right eye, the temporal portion of the retina of the left eye, lateral to the fovea, contains photoreceptors recognizing wavelengths from approximately 525 nm to approximately 700 nm, while the nasal portion of the retina of the left eye, medial to the fovea, contains photoreceptors recognizing wavelengths from approximately 400 nm to 525 nm.

In any event, the approximate location of photoreceptors on the retina 118 recognizing particular frequencies of light are set forth in Tables A and B, as described based on their approximate relative distances from the fovea 124 in a 1× scale of the human eye.

TABLE A

| Wavelength of Light Recognized (nm) | Distance Medial to the Fovea (mm) |
| --- | --- |
| 375 | 11.625 |
| 410 | 7.625 |
| 425 | 6.375 |
| 480 | 3.5 |
| 500 | 2.25 |
| Normal Focal Point | 0.75 |

TABLE B

| Wavelength of Light Recognized (nm) | Distance Lateral to the Fovea (mm) |
| --- | --- |
| 540 | 5.875 |
| 560 | 6.75 |
| 580 | 8 |
| 600 | 9.25 |
| 700 | 13.875 |

Figure 4B:
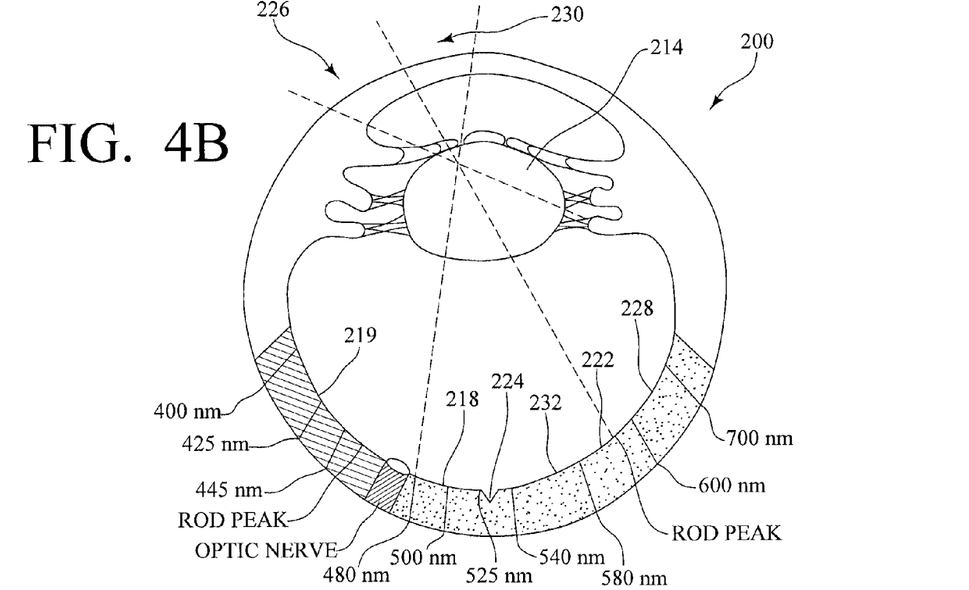
FIG. 4B is a cross-sectional representation of an eye having a shifted lens, illustrating the areas of the retina capable of receiving light.

When light enters and moves through an eye 200 having a shifted lens 214, it is directed through the lens 214 such that it only reaches certain portions of the retina 218. For example, with reference to FIG. 4B depicting a lens 214 shifted approximately 24-25 degrees medial to the optic axis of the eye 200, light entering the eye 200 is directed to a focal point 222, which is shifted to a location lateral to the fovea 224. Light entering from the nasal field 226 is directed to a portion 228 of the retina 218 lateral to the focal point 222. Similarly, light entering from a temporal field 230 is directed to a portion 232 of the retina 218 medial to the focal point 222.

The refraction of light by the crystalline lens 214 causes a refraction pattern that results in light failing to be directed towards certain photoreceptors in an eclipsed area 219. Additionally, certain areas of the retina 218 and photoreceptors associated with those areas may become over-stimulated or under-stimulated because of the altered refraction pattern formed by the shifted lens 214.

In the eye 200 depicted in FIG. 4B, the lens 214 is shifted medial to the optic axis, resulting in an the area 219 medial the optic nerve 233 being substantially eclipsed, the area 219 containing photoreceptors recognizing light of wavelengths from approximately 400 to 475 nm. Although the shifting of the focal point causes certain redirection of light, it is primarily the shifting of the stacked prism structure of the lens, causing a jumbled refraction pattern, that results in the eclipsing of an area of the retina. Of course, depending on the degree of ocular asymmetry and the shifting of the lens to various degrees either medial or lateral to the optic axis, different areas of the retina 218 could become substantially eclipsed, under-stimulated or over stimulated.

Figure 5A:
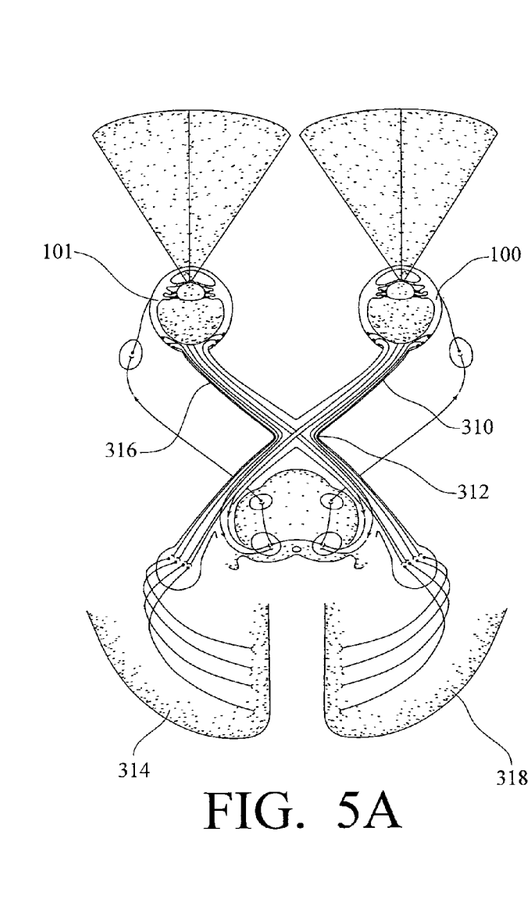
FIG. 5A is a schematic diagram illustrating the communication of normal eyes with the optic pathways and the brain.

Turning now to FIG. 5A, the manner in which light is thought to enter and travel through the normal eye 100, 101 for conversion into the electrical impulses which are ultimately sent to the brain will now be described. Electrical impulses from the photoreceptors of the right eye 100 are transmitted through the optic nerve 310 and through the optic chiasm 312 where signals are diverted to the left occipital lobe 314. Similarly, electrical impulses from the photoreceptors of the left eye 101 are transmitted through the optic nerve 316 and through the optic chiasm 312 where signals are diverted to the right occipital lobe 318.

In an individual with an eye 200 having a shifted lens 214, the electrical impulses sent to the brain from the eyes 200, 201 do not coordinate. For example, with reference to FIG. 5B, normal electrical impulses from the photoreceptors of the left eye 201 are transmitted through the optic nerve 416 and through the optic chiasm 412 where signals are diverted to the right occipital lobe 418. In the right eye 200 having a shifted lens 214, electrical impulses from only the photoreceptors that are not eclipsed in the right eye 200 are transmitted through the optic nerve 410 and through the optic chiasm 412 where signals are diverted to the left occipital lobe 414. As such, the information received by the left occipital lobe 414 does not coordinate with the information received by the right occipital lobe 418. That is to say, light directed, for example, to the focal point of the left eye is received by photoreceptors medial to the fovea, while light directed to the focal point of the right eye is received by photoreceptors lateral to the fovea, which location on the retina and associated photoreceptors are not corresponding.

Figure 5B:
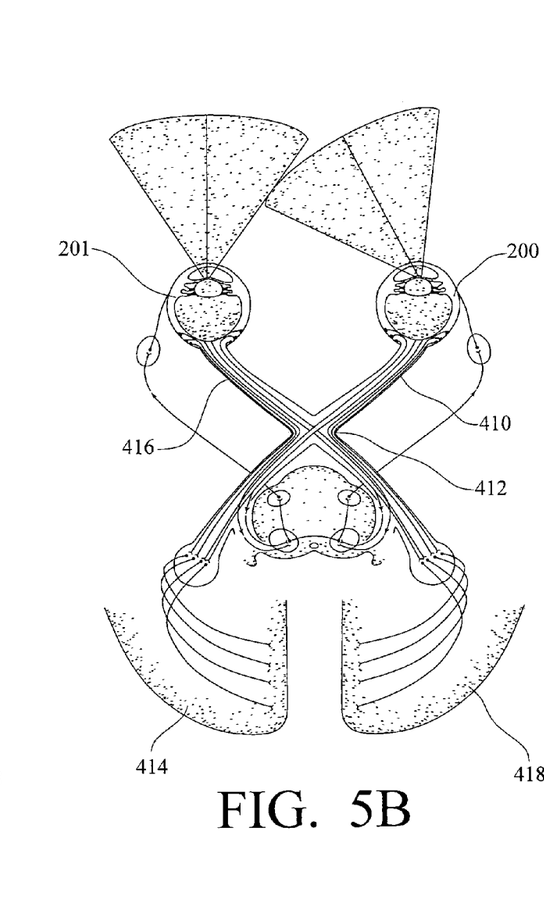
FIG. 5B is a schematic diagram illustrating the communication of a normal eye and an eye having a shifted lens with the optic pathways and the brain.

In the eyes 200 depicted in FIGS. 4B and 5B, the lens 214 is shifted medial to the optic axis, generally resulting in a particular area 219 or areas medial the fovea 224 being substantially eclipsed. Generally, if a lens is shifted medial to the optic axis of the eye, an area medial the fovea may become substantially eclipsed, and if a lens is shifted lateral to the optic axis of the eye, an area lateral the fovea may become substantially eclipsed. Of course, the lens could be shifted to various degrees either medial or lateral to the optic axis, resulting in different areas of the retina 218 becoming substantially eclipsed, under-stimulated or over stimulated, which might explain varying types of learning differences.

Without wishing to be bound by theory or mechanism, it is thought that various learning differences resulting in difficulties with reading and comprehension are characterized by a right eye having a lens shifted by varying degrees medial to the optic axis. Such learning differences have also been observed to be accompanied by high dopamine levels and low serotonin levels. It is further thought that various learning differences resulting in difficulties with math and in behavioral difficulties are characterized by a left eye having a lens shifted by varying degrees medial to the optic axis. Such learning differences have also been observed to be accompanied by high serotonin levels and low dopamine levels. It is further thought that various learning differences may result based on shifting in one or both eyes of an individual, for example, a left and/or right eye shifting lateral to the optic axis.

In any event, as the brain receives data from the right and left eyes, it compares the data to insure the information is properly decoded and interpretations are made such as stereopsis, the single perception of a slightly different image received from each eye. The brain relies on receiving compatible signals from the corresponding photoreceptor through the optic nerve to the correct location of the visual cortex. When incompatible data is received, the visual cortex must compensate by blocking or processing the data in other areas of the brain resulting in data interpolation delays and errors that may result in dyslexia and other learning differences.

For example, the normal lens directs images to the retina that are inverted and reversed, which the brain perceives as normal. However, when the eyes are directing incompatible images on to the retina, as the brain attempts to resolve the images, it may rely more heavily on information received from one eye, a dominant eye. The eye may perceive that it is in a monocular viewing environment, rather than a binocular viewing environment, and fail to appropriately translate the inverted and reversed images received. Such a perception, in the exemplary case of dyslexia, may result in letter reversal such as "b & d" or "p & q", along with sight word blindness and a blue color weakness, perhaps because an area of the retina containing photoreceptors recognizing wavelengths from approximately 400 nm to approximately 475 nm is eclipsed.

Figure 6:
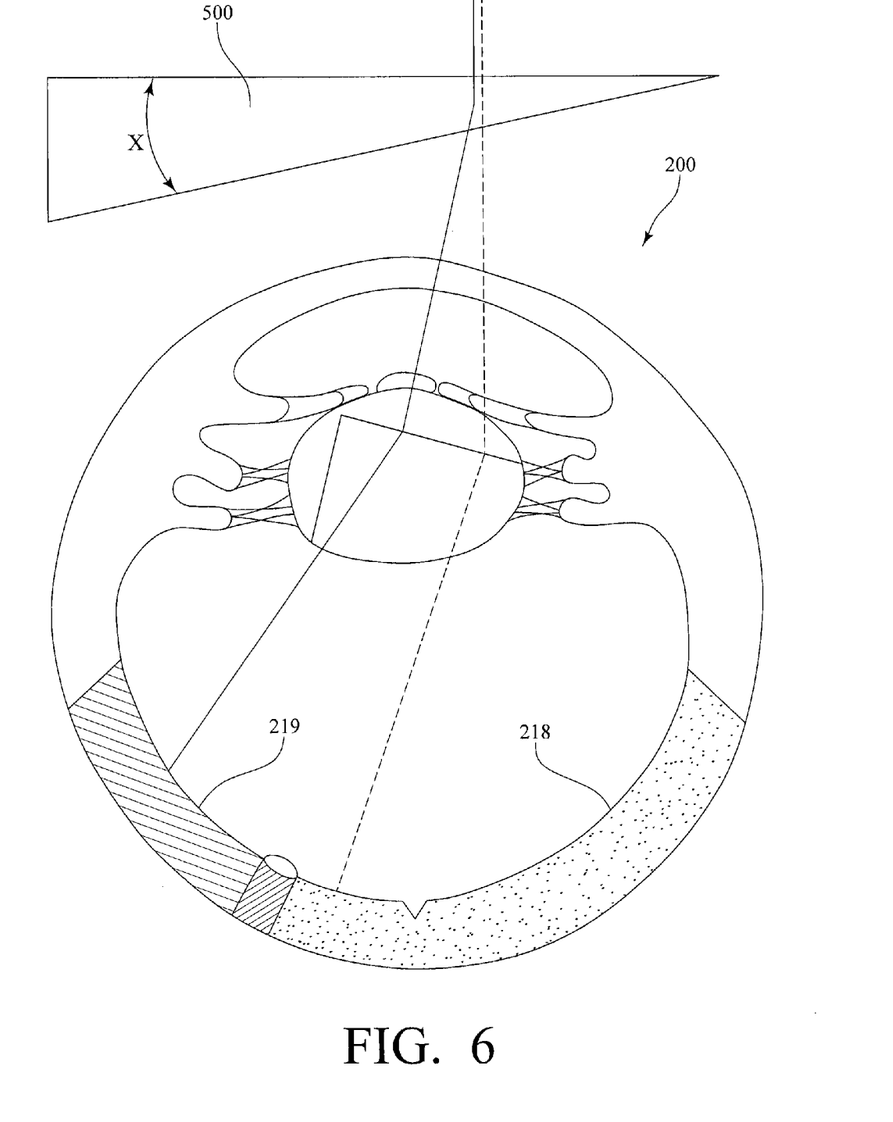
FIG. 6 is a cross-sectional representation similar to that of FIG. 4B, illustrating the redirection of light to the eclipsed area of the retina using an exemplary apparatus and method of the present invention.

The apparatus and method of the present invention redirects light entering an eye having a shifted lens such that eclipsed areas of the retina are activated and correction is made for any under-stimulation or over-stimulation of areas. With reference to FIG. 6, an exemplary apparatus of the present invention includes a prism lens 500 placed adjacent the eye 200 such that light entering the eye 200 is redirected. For purposes of this application, a prism lens is a lens, with sides that converge at an angle X that refracts light in a predetermined direction. Light entering the eye 200 without the aide of the prism lens 500, represented by the dotted-lined arrow, is not directed to the eclipsed area 219 of the retina 218; however, light entering the eye 200 after being redirected by the prism lens 500, represented by the solid-lined arrow, is directed toward the eclipsed area 219.

Because the eclipsed area 219 of the retina 218 could vary depending, for example, on the degree of facial asymmetry, which is thought to correlate to a particular type of learning difference, the prism lens 500 may be designed to direct light specifically to the eclipsed area 219 of the retina 218 of the individual 10 being treated. For example, the prism lens 500 may be designed to have an angle X between approximately two- and twenty-degrees. For another example, the prism lens 500 may have an angle X between approximately four- and eleven-degrees. For another example, the prism lens 500 may have an angle X between approximately five- and nine-degrees.

Figure 10:
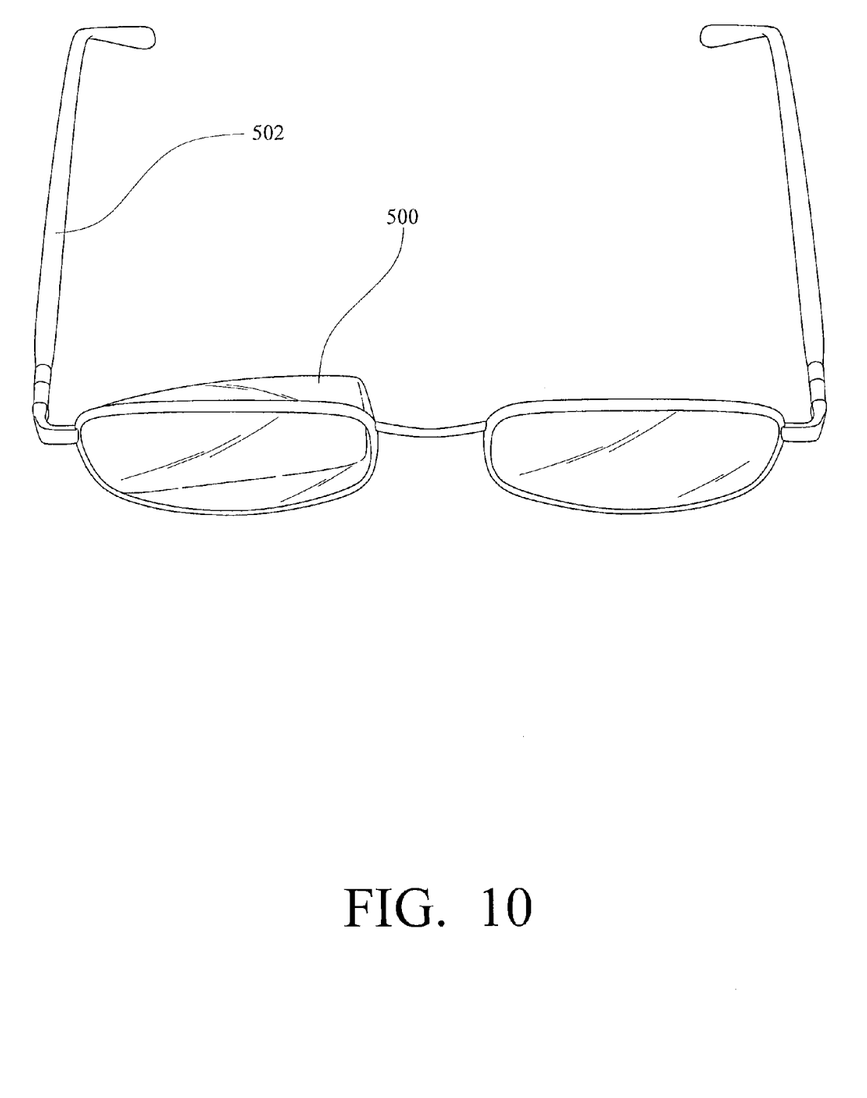
FIG. 10 is an exemplary apparatus of the present invention.

The prism lens 500 may be adapted in a variety of manners to facilitate the ease with which it is used. In this regard, means for positioning the lens 500 adjacent the eye 200 may be provided. For example, with reference to FIG. 10, a bracket 502 may be secured to the prism lens 500 and adapted such that the prism lens 500 is positioned adjacent the eye 200 in an orientation such that it tends to direct light toward the eclipsed area 219. The bracket 502 may be structured similarly to a pair of eyeglasses, which are fitted with the prism lens 500, as shown in FIG. 10; however, the bracket could have a more simple or more complex design without departing from the spirit and scope of the present invention. Alternatively, the lens could be positioned adjacent the eye using a contact lens, which has been designed to direct light as a prism lens 500 of the present invention. Additionally, an artificial lens could be designed and implanted surgically to achieve the same effect without departing from the spirit and scope of the present invention.

By using the prism lens 500 to redirect light to the eclipsed area 219 of the retina 218, the area 219 is activated, in that light is directed towards the photoreceptors in that area 219, altering the electrical impulses directed through the optic pathways to the brain. The results experienced using the apparatus and method of the present invention will differ based on the learning difference being treated. For example, in the case of dyslexia, redirection of light may cause improvements in reading by correcting inversions and reversals of letters or words. For another example, in the case of difficulties with night vision and depth perception, the redirection of light may improve night vision dark adaptation and depth perception with various color hues noted which were not previously perceived. Additionally, differences in color perception and recognition may be experienced. Of course, more and different learning differences could be treated using the apparatus and method of the present invention.

Figure 7:
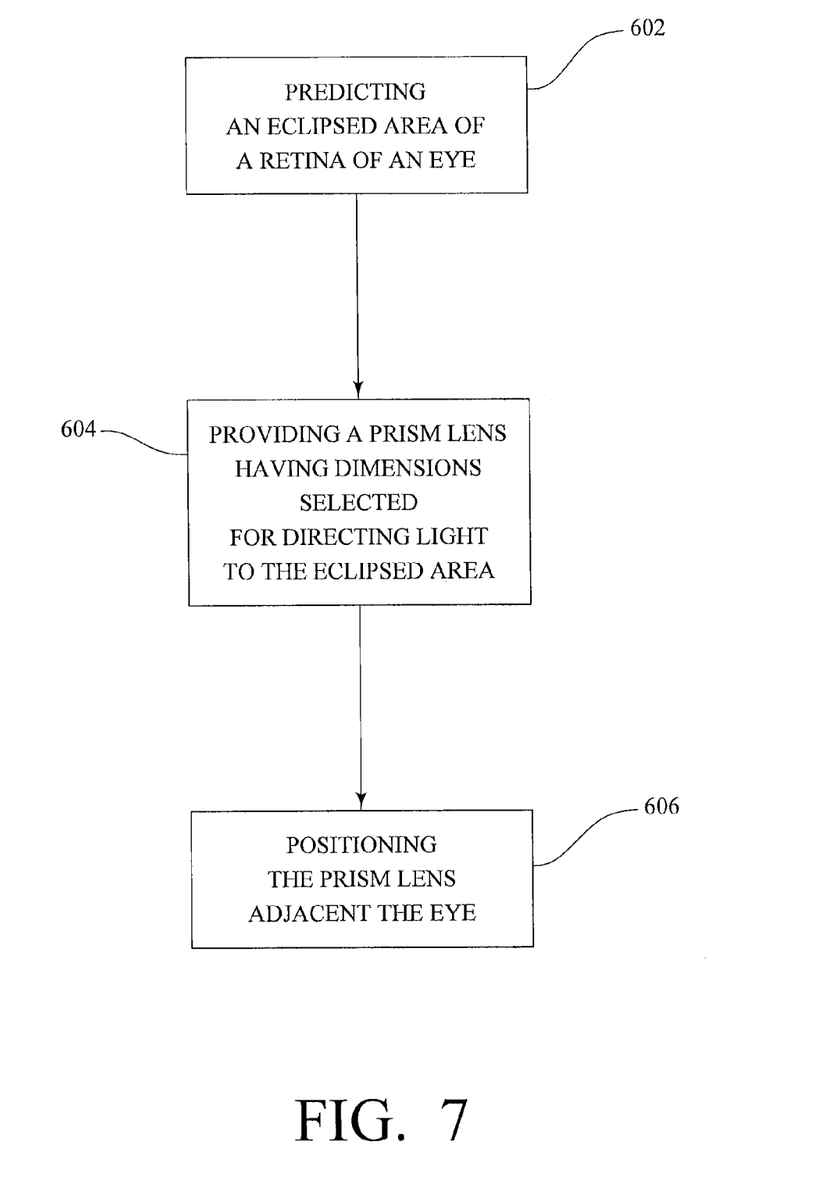
FIG. 7 is a flow chart illustrating the steps involved in an exemplary implementation of the method of the present invention.

The method for treating learning differences of the present invention will now be described. With reference to FIG. 7, an exemplary method of the present invention includes: predicting an eclipsed area of a retina of an eye of the individual 602; providing a prism lens having dimensions selected for directing light to the eclipsed area 604; and positioning the prism lens adjacent the eye 606.

With regard to the step of predicting an eclipsed area of a retina of an eye 602, generally, a non-dominant eye in a binocular viewing environment is the eye having a shifted lens and therefore an eclipsed area of the retina. In this regard, the non-dominant eye is generally the appropriate eye to be treated. The following is an exemplary manner in which the non-dominant eye may be identified.

Although the human eyes generally work together, there are limits in which a binocular vision system is in full activation. The binocular vision system is in full activation when viewing objects between about 6 inches to about 200 feet from the face. At less than about 6 inches from the face, the eyes function as independent monocular vision systems. As such, there are two viewing environments: the monocular viewing environment, wherein the viewing point is less than about 6 inches from the face; and the binocular viewing environment, wherein the viewing point is greater than about 6 inches from the face.

In a monocular viewing environment, one eye is substantially dominant in that it is the eye which is primarily used to transmit the light that is converted to electrical impulses ultimately received by the visual cortex of the brain where the sensation of vision occurs. When moving into a binocular viewing environment, the dominant often switches, but one eye is substantially dominant in that it is the eye that remains in substantial alignment with the object being viewed, while the non-dominant eye defers to the dominant eye.

Monocular Ocular Dominance Test: A pattern of ocular dominance is established by identifying the dominant eye over a series of focal points. The ocular dominance at less than about 6 inches may be determined, for example, by requesting the individual being treated to pick up a tube, a kaleidoscope, or other item having a view finder that requires the individual to select one eye to align with the view finder. The individual will tend to align the view finder with the monocular dominant eye.

Binocular Ocular Dominance Test: The ocular dominance at more than about 6 inches may be determined, for example, by requesting that the individual hold a frame having an open center or a circle formed with his or her fingers at a distance of more than about 6 inches, e.g., 7 to 18 inches. The individual will then be requested to look through the frame with both eyes; however, the individual will tend to align the frame with the binocular dominant eye.

Squint Test: Another test used to identify the eye that should receive the prism lens is conducted by requesting that the individual look into a light with both eyes. Because the shifting of the lens in an eye may cause over-stimulation of photoreceptors in certain areas of the retina, the individual will tend to squint the eye having the shifted lens.

Concentrated Writing Test: Another test used to identify the eye that should receive the prism lens is conducted by asking which hand the individual writes with ("handedness") and requesting that the individual perform a concentrated act of writing. If, while concentrating, the individual is right handed and holds the writing implement with the third finger and thumb or between the third and ring fingers, the left eye tends to be dominant indicating that the right eye has a shifted lens. If the right-handed individual holds the writing implement with the index finger and thumb or between the third and index finger, the right eye tends to be dominant indicating that the left eye has a shifted lens. Similarly, if the individual is left handed and holds the writing implement with the third finger and thumb or between the third and ring fingers, the right eye tends to be dominant indicating that the left eye has a shifted lens. If the left-handed individual holds the writing implement with the index finger and thumb or between the third and index finger, the left eye tends to be dominant indicating that the right eye has a shifted lens.

Subject Preference Inquiry: Another inquiry that provides information for identifying the eye that should receive the prism lens is whether the individual prefers reading or math. Individuals having difficulty reading tend to have a shifted lens in the right eye, while individuals having difficulty in math tend to have a shifted lens in the left eye.

Facial Asymmetry Ratio Inquiry: Additionally or alternatively, the facial asymmetry ratio R of the individual is measured and used to identify the dominant eye. Referring again to Equation (1), when R is a positive number, i.e., when the left eye is anatomically closer to the mid-line of the face, the right eye tends to be dominant in the monocular viewing environment at about 0 to 6 inches while the left eye tends to be dominant in the in the binocular viewing environment beyond about 6 inches. Such is the case with individuals having certain forms of dyslexia; as such, the right eye, as the non-dominant eye, should be selected to receive the lens. Depending on the learning difference, the ocular pattern of dominance and the facial asymmetry ratio R of the individual being treated, a different or both eyes may be selected to receive a lens without departing from the spirit and scope of the present invention.

With regard to predicting whether the eclipsed area is medial or lateral to the fovea, if the lens is shifted medial to the optic axis, the eclipsed area will tend to be medial the fovea, and if the lens is shifted lateral to the optic axis, the eclipsed area will tend to be lateral the fovea. There are certain factors which may assist in making this prediction, including the following examples.

Horizontal Strabismus Inquiry: In certain individuals, in addition to a shifted lens, there may be a horizontal strabismus in the same direction as the shifting of the lens, which horizontal strabismus may be apparent when looking at the individual.

Color Preference Inquiry: Another inquiry that provides information for predicting the location of the eclipsed area involves requesting information about the individuals favorite color or colors. As described above with reference to FIG. 4A, it is thought that photoreceptors recognizing wavelengths from approximately 525 nm to approximately 700 nm, and therefore certain lower frequency greens, yellows, oranges and reds, are located lateral to the fovea, while photoreceptors recognizing wavelengths from approximately 400 nm to approximately 525 nm, and therefore violet, indigo, blue, and certain higher frequency greens, are located medial to the fovea. As such, individuals having an eclipsed area lateral to the fovea tend to chose blues, indigos and violets as favorite colors, while individuals having an eclipsed area medial to the fovea tend to chose reds, oranges and yellows as favorite colors.

Generally, more than one of the above tests and/or inquiries is made and the resulting data is compiled. Pieces of incompatible data may be overlooked if the overall data tends to indicate that a particular prediction should be made, i.e., each individual test may not be predictive in and of itself for a particular individual; however, by administering multiple tests and making multiple inquiries, a trend may be established.

Figure 8:
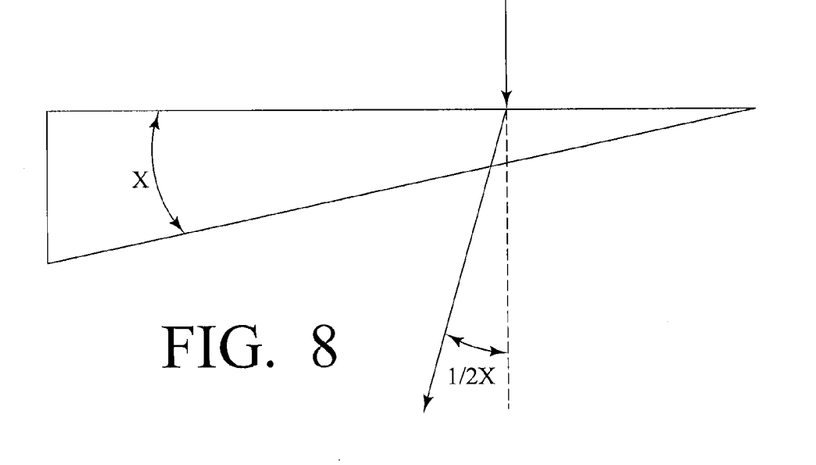
FIG. 8 is a schematic view of an exemplary apparatus of the present invention.
Figure 9:
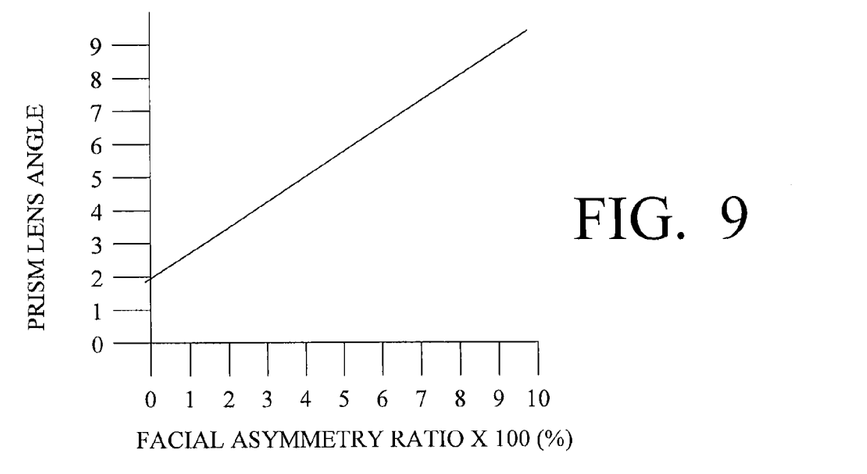
FIG. 9 is an standard curve plotting prism angle as a function of facial asymmetry ratio in accordance with the method of the present invention.

Turning now to the step of providing a prism lens selected for redirecting light entering an eye 604, the prism lenses of the present invention may redirect light at a variety of different angles. For example, with reference to FIG. 8, if a prism lens 500 refracts light at an angle of 4 degrees, it can be described as having an angle of 8 degrees, i.e., a lens refracting light at an angle of ½X degrees, can be described has having an angle of X degrees. The angle and orientation of the lens for redirecting light entering the eye of the individual being treated will vary depending on the location of the eclipsed area of the retina. Lenses having varying angles may be tested on the individual until one is identified which has a beneficial result, e.g., in the case of certain forms of dyslexia thought to be characterized by an eclipsed region medial to the fovea in the right eye, individuals may experience enhanced "blue" color perception and recognition and enhanced reading and comprehension skills. In this regard, sequential testing of various lenses in various orientations until one is identified having a beneficial result is a method that may be used to predict the location of the eclipsed area and provide a prism lens selected for redirecting entering the eye. Some beneficial results may be experienced immediately upon use of the prism lens and other results may be experienced after extended use of the prism lens. As an alternative, or in addition to trial-and-error-based selection of a prism lens angle, a standard curve may be used, such as the one shown in FIG. 9 plotting prism angle as a function of facial asymmetry ratio. The facial asymmetry ratio of the individual being treated may correlate to the presence of certain learning differences, individuals may be identified for treatment by calculating a facial asymmetry ratio for the individuals, as described above.

With regard to the step of positioning the prism lens adjacent the eye 606, the prism lens should be oriented such that it tends to direct light toward the eclipsed area of the retina. When the photoreceptors in the eclipsed area are activated, a signal from the eye receiving the lens becomes compatible or synchronous with the signal transmitted by the other eye. As such, the brain begins receiving compatible data from the two eyes of the individual and no longer must attempt to fuse two incompatible sets of data. Such synchronicity of data alleviates any previously experienced interference patterns of excitation in the visual cortex which resulted in symptoms associated with learning differences. Without wishing to be bound by theory or mechanism, in the case of an individual having certain forms of dyslexia characterized by damage to the magnocellular and parvocellular pathways leading to the back left part of the brain, the redirection of light by the prism lens through the right eye leads to reactivation of the back left portion of the brain, placing it in synchrony with the back right portion of the brain.

The efficacy of the apparatus and method of the present invention will now be illustrated by the following prophetic, specific but non-limiting example.

EFFICACY EXAMPLE

An individual having a learning difference is identified and administered the tests of the Wechler Intelligence Scale for Children (WISC). See e.g., D. J. Reschley & J. P. Grimes, *Best Practices in School Psychology III: Intellectual Assessment* (1995): J. M. Sattler, *Assessment of Children*, 3d Ed., (1992); A. S. Kaufman, *Intelligence Testing with the WISC-III* (1994). The individual receives the scores set forth in Table B under the heading "First Administration."

A non-dominant eye of the individual is identified, appropriate dimensions of a prism lens are selected and the prism lens is placed adjacent the non-dominant eye. The individual uses the prism lens for reading and comprehension activities for about 3 months and the WISC is readministered. The individual receives the scores set forth in Table B under the heading "Second Administration."

TABLE B

| Category | First Administration | Second Administration |
| --- | --- | --- |
| Block Design | | |
| Raw Score | 18 | 30 |
| Standard Score | 1 | 6 |
| # of rotations/reversals | 3 | 1 |
| Coding | | |
| Raw Score | 17 | 47 |
| Standard Score | 1 | 6 |
| # of rotations/reversals | 8 | 2 |
| Symbol Search | | |
| Raw Score | 9 | 28 |
| Standard Score | 1 | 8 |
| # of errors | 6 | 2 |
| Processing Speed Index | 50 | 83 |

As shown by the improved scores following the second administration of the tests, treatment using an embodiment of the apparatus and method of the present invention results in alleviation of symptoms associated with the learning difference.

Unless otherwise indicated, all numbers expressing quantities used herein are to be understood as being modified in all instances by the term "about." Accordingly, unless indicated to the contrary, the numerical parameters set forth in the Specification and Claims are approximations that may vary depending upon the desired results sought by the present invention.

It will be obvious to those skilled in the art that further modifications may be made to the embodiments described herein without departing from the spirit and scope of the present invention.

What is claimed is:

1. A method for treating a learning difference of an individual, comprising the steps of:
predicting a location of an eclipsed area of a retina of an eye of the individual;
providing a prism lens having dimensions selected for directing light to the eclipsed area; and positioning the prism lens adjacent the eye such that light is directed to the eclipsed area of the retina, thereby alleviating symptoms of the learning difference.

2. The method of claim 1, wherein the step of predicting the location of the eclipsed area is facilitated by administering or making at least one test or inquiry selected from: Monocular Ocular Dominance Test; Binocular Ocular Dominance Test; Squint Test; Concentrated Writing Test; Subject Preference Inquiry; and Facial Asymmetry Ratio Inquiry.

3. The method of claim 2, wherein the step of predicting the location of the eclipsed area is additionally facilitated by making at least one inquiry selected from: Horizontal Strabismus Inquiry; and Color Preference Inquiry.

4. The method of claim 1, wherein the step of predicting the location of the eclipsed area is facilitated by administering or making at least two tests or inquiries selected from: Monocular Ocular Dominance Test; Binocular Ocular Dominance Test; Squint Test; Concentrated Writing Test; Subject Preference Inquiry; Facial Asymmetry Ratio Inquiry; Horizontal Strabismus Inquiry; and Color Preference Inquiry.

5. The method of claim 1, wherein the step of predicting the location of the eclipsed area includes identifying the non-dominant eye.

6. The method of claim 5, wherein the step of predicting the location of the eclipsed area further includes determining whether the eclipsed area is medial or lateral to a fovea in the non-dominant eye.

7. The method of claim 1, wherein the step of predicting the location of the eclipsed area includes identifying the eye having a shifted lens.

8. The method of claim 7, wherein the step of predicting the location of the eclipsed area further includes determining whether the eclipsed area is medial or lateral to a fovea of the eye having the shifted lens.

9. The method of claim 1, wherein the step of providing the prism lens having selected dimensions includes testing lenses of various dimensions until one produces beneficial result.

10. The method of claim 1, wherein the steps of predicting the eclipsed area and providing the prism lens having selected dimensions each include testing lenses of various dimensions until one produces beneficial result.

11. The method of claim 1, wherein the eclipsed area includes photoreceptors capable of recognizing light having wavelengths between approximately 400 nm and approximately 475 nm.

12. The method of claim 1, wherein the eclipsed area includes photoreceptors capable of recognizing light having wavelengths between approximately 540 nm and approximately 700 nm.

13. The method of claim 1, wherein the prism lens has dimensions selected for directing light to an area of the retina between approximately 3.7 mm and approximately 11.67 mm medial to a fovea.

14. The method of claim 1, wherein the prism lens has dimensions selected for directing light to an area of the retina between approximately 5.9 mm and approximately 13.9 mm lateral to a fovea.

15. The method of claim 1, wherein the prism lens has sides that converge at an angle between approximately 2 and approximately 20 degrees.

16. A method for treating a learning difference of an individual, comprising the steps of:
  predicting at least one area of a retina of an eye of the individual characterized as an over-stimulated area, an under-stimulated area, or an eclipsed area;
  providing a prism lens having dimensions selected for directing light to the at least one area; and
  positioning the prism lens adjacent the eye such that light is directed to the at least one area of the retina, thereby alleviating symptoms of the learning difference.

17. An apparatus for treating a learning difference of an individual, comprising:
  a prism lens for directing light to an eclipsed area of a retina of an eye of the individual; and
  a means for positioning said prism lens adjacent the eye such that light is directed to a predicted location of the eclipsed area of the retina to address the learning difference.

18. The apparatus of claim 17, wherein the means for positioning is a bracket.

19. The apparatus of claim 17, wherein the prism lens has dimensions selected for directing light to an area of the retina between approximately 3.7 mm and approximately 11.67 mm medial to a fovea.

20. The apparatus of claim 19, wherein the prism lens has sides that converge at an angle between approximately 2 and approximately 20 degrees.

21. The apparatus of claim 17, wherein the prism lens has dimensions selected for directing light to an area of the retina between approximately 5.9 mm and approximately 13.9 mm lateral to a fovea.

* * * * *